US005693586A

United States Patent [19]
Nicolau et al.

[11] Patent Number: 5,693,586
[45] Date of Patent: Dec. 2, 1997

[54] PALLADIUM-GOLD CATALYST FOR VINYL ACETATE PRODUCTION

[75] Inventors: Ioan Nicolau; Philip M. Colling; Leland R. Johnson, all of Corpus Christi, Tex.

[73] Assignee: Hoechst Celanese Corporation, Warren, N.J.

[21] Appl. No.: 670,860

[22] Filed: Jun. 28, 1996

[51] Int. Cl.$^6$ .............................. B01J 23/44; B01J 23/52
[52] U.S. Cl. .................... 502/330; 502/325; 502/344
[58] Field of Search ..................... 502/325, 330, 502/344

[56] References Cited

U.S. PATENT DOCUMENTS

| | | | |
|---|---|---|---|
| 3,761,513 | 9/1973 | Sennewald et al. | 260/497 |
| 3,775,342 | 11/1973 | Kronig et al. | 252/430 |
| 3,822,308 | 7/1974 | Kronig | 260/497 |
| 3,939,199 | 2/1976 | Fernholz et al. | 260/469 |
| 4,048,096 | 9/1977 | Bissot | 252/430 |
| 4,087,622 | 5/1978 | Nakamura et al. | 560/245 |
| 4,133,962 | 1/1979 | Fernholz et al. | 560/245 |
| 4,902,823 | 2/1990 | Wunder et al. | 560/245 |
| 5,179,056 | 1/1993 | Bartley | 502/170 |
| 5,179,057 | 1/1993 | Bartley | 502/170 |
| 5,194,417 | 3/1993 | Smith et al. | 502/330 |
| 5,258,340 | 11/1993 | Augustine et al. | 502/60 |
| 5,314,858 | 5/1994 | Colling et al. | 502/330 |
| 5,332,710 | 7/1994 | Nicolau et al. | 502/243 |
| 5,422,329 | 6/1995 | Wirtz et al. | 502/328 |
| 5,466,652 | 11/1995 | Paparizos et al. | 502/330 |

*Primary Examiner*—Walter D. Griffin
*Assistant Examiner*—Nadine Preisch
*Attorney, Agent, or Firm*—M. Susan Spiering; Donald R. Cassady

[57] ABSTRACT

This invention provides a supported palladium-gold catalyst for vinyl acetate production from ethylene, acetic acid and oxygen. All of the reactants employed in the catalyst preparation are potassium salt compounds which are essentially sodium-free. A preferred invention palladium-gold catalyst provides exceptional improvement of carbon dioxide selectivity in vinyl acetate production.

20 Claims, No Drawings

PALLADIUM-GOLD CATALYST FOR VINYL ACETATE PRODUCTION

BACKGROUND OF THE INVENTION

This invention relates to a novel process for the preparation of a palladium-gold catalyst with improved selectivity in vinyl acetate production.

A well-known commercial process for the production of vinyl acetate is by the gas phase reaction of ethylene, acetic acid and oxygen in the presence of a supported catalyst which contains palladium.

A preferred type of vinyl acetate catalyst is one having a content of palladium metal and gold metal distributed on the surface of a support substrate such as silica or alumina.

Prior art references which describe supported palladium-gold catalysts for vinyl acetate production include U.S. Pat. Nos. 3,761,513; 3,775,342; 3,822,308; 3,939,199; 4,048,096; 4,087,622; 4,133,962; 4,902,823; 5,179,056; 5,179,057; 5,194,417; 5,314,858; 5,332,710; and references cited therein; incorporated by reference.

A standard process for preparing a vinyl acetate catalyst containing palladium and gold deposited on a catalyst support medium comprises (1) impregnating the support with an aqueous solution of water-soluble palladium and gold compounds, (2) precipitating and fixing water-insoluble palladium and gold compounds on the catalyst support by contacting the impregnated catalyst support with an aqueous alkaline solution capable of reacting with the water-soluble palladium and gold compounds to form the water-insoluble precious metal compounds, (3) washing the treated catalyst with water to remove anions which are freed from the initially impregnated palladium and gold compounds during precipitation, and (4) converting the water-insoluble palladium and gold compounds to the free metal state by treatment with a reducing agent. An optional final procedure usually involves (5) impregnating the reduced catalyst with an aqueous alkali metal alkanoate solution, and drying the final catalyst product.

The activity and selectivity properties of a supported palladium-gold catalyst are affected by the physicochemical form of the palladium and gold metal content on the catalyst support substrate.

U.S. Pat. No. 4,048,096 describes a catalyst which consists of a palladium-gold alloy distributed as a shell coating on the exterior surface area of a catalyst support such as porous silica. The shell distribution of palladium-gold alloy provides an improved space-time-yield activity in a vapor phase reaction of ethylene, acetic acid and oxygen for vinyl acetate production.

The selectivity of a palladium-gold catalyst in vinyl acetate synthesis also is influenced by the extent and uniformity of the palladium metal and gold metal distribution on the exterior and/or interior surfaces of a porous catalyst support substrate, such as carbon dioxide selectivity and oxygen conversion in an ethylene, acetic acid and oxygen vapor phase reaction.

Attempts to provide a uniform distribution of the palladium and gold metals on the catalyst support has involved manipulation of the catalyst preparation steps and/or by using support substrates having various specified pore dimensions. Particularly useful improvements in preparing highly active catalysts for vinyl acetate production are disclosed in U.S. Pat. No. 5,314,858 and U.S. Pat. No. 5,332,710. These references describe process embodiments for improving palladium and gold distribution on a support by manipulating the precipitation step in which the water-soluble precious metal compounds are fixed to the support surface as water-insoluble compounds. In U.S. Pat. No. 5,314,858, fixing precious metals on the support is achieved utilizing two separate precipitation stages to avoid using large excesses of fixing agent. U.S. Pat. No. 5,332,710 describes fixing the precious metals by physically rotating an impregnated catalyst support while the impregnated support is immersed in a reaction solution at least during the initial precipitation period. The novel rotation immersion procedure yields catalysts in which the precipitated carrier metals are more evenly distributed in a thin shell on the support surface.

The prior art has addressed other physicochemical aspects that affect the properties of palladium gold catalysts which are adapted for vinyl acetate production.

U.S. Pat. No. 5,179,056 and U.S. Pat. No. 5,179,057 are related references which are directed to the improvement palladium-gold catalysts for vinyl acetate production from ethylene, acetic acid and oxygen. The described invention catalysts have increased activity because of a reduced sodium content.

In a preferred catalyst preparation embodiment of the two references, the sodium content of a supported palladium-gold is reduced during catalyst preparation by washing the palladium and gold metal-containing support medium with an ion-exchange aqueous solution of a potassium compound. In the catalyst preparation processes of the two references, the use of precious metal sodium salt compounds is permitted, such as sodium palladium tetrachlorate ($Na_2PdCl_4$). The added sodium content in the precious metal-treated catalyst support substrate subsequently is removed by washing with an aqueous ion-exchange solution.

There is a continuing interest in the development of catalyst compositions which exhibit an improved combination of properties for the production of vinyl acetate.

Accordingly, it is an object of this invention to provide a supported palladium-gold catalyst composition with improved carbon dioxide selectivity in vinyl acetate production from ethylene, acetic acid and oxygen.

It is another object of this invention to provide a supported vinyl acetate catalyst which is essentially sodium-free, and is characterized by a thin palladium-gold metal shell coating on the support surface.

It is a further object of this invention to provide a process for preparation of a supported palladium-gold catalyst for vinyl acetate production from ethylene, acetic acid and oxygen, in which process all of the catalyst support-impregnating reactants are essentially sodium-free potassium salt compounds.

Other objects and advantages of the present invention shall become apparent from the accompanying description and examples.

DESCRIPTION OF THE INVENTION

One or more objects of the present invention are accomplished by the provision of a process for the preparation of a catalyst for production of vinyl acetate from ethylene, acetic acid and oxygen, which process comprises (1) impregnating a porous catalyst support medium with an aqueous solution of water-soluble potassium-palladium compound and water-soluble potassium-gold compound; (2) precipitating water-insoluble palladium and gold compounds onto the catalyst support surface with an aqueous solution of basic potassium salt fixing agent; and (3) reducing the water-insoluble palladium and gold compounds to palladium metal and gold metal to form a catalyst with improved carbon dioxide selectivity.

The catalyst support medium is selected from porous substrates such as silica, alumina, silica/alumina, or titania, in the form of spheres, tablets, Raschig rings, and the like. For purposes of the present invention, it is preferred that the support medium has little or no content of sodium, i.e., a sodium content less than about 0.1 weight percent of the support medium.

A typical catalyst support medium is illustrated by porous silica spheres which have a radius of 1–8 mm, a pore volume of 0.1–2 cc/g, and an internal surface area of 10–350 m$^2$/g. Commercial catalyst support media are widely available, such as porous 5 mm silica spheres sold under the tradename KA-160 by Sud-Chemie.

In one method of preparing the improved vinyl acetate catalyst of the present invention, the catalyst support first is impregnated with an aqueous solution of water-soluble potassium-palladium compound and potassium-gold compound. Suitable water-soluble palladium and gold compounds are illustrated by potassium palladium tetrachlorate ($K_2PdCl_4$) and potassium tetrachloroaurate ($KAuCl_4$).

The volume of the aqueous impregnating solution preferably is between about 95–100% of the absorptive capacity of the catalyst support, which is characterized as an "incipient wetness" technique. As an alternative procedure, the water-soluble potassium-palladium compound and the potassium gold compound respectively can be impregnated on the support successively in separate aqueous solutions.

In step (2) of the invention process, in accordance with a standard method the impregnated catalyst support is treated with an aqueous solution of a basic potassium salt, such as potassium silicate, potassium carbonate or potassium hydroxide. The treatment with basic potassium salt solution fixes the palladium and gold compounds on the catalyst support, i.e., palladium hydroxide and gold hydroxide are precipitated and are incorporated onto the catalyst support surface.

The amount of basic potassium salt fixing agent employed in step (2) of the invention process is such that the ratio of potassium metal to anions from the water-soluble precious metal compounds is from about 1:1 to about 2:1, preferably from about 1.2:1 to about 1.8:1. By treatment with the basic potassium salt solution, the precious metal water-soluble compounds are converted to water-insoluble compounds which mainly appear to be hydroxides and/or oxides.

Another method of palladium and gold fixing agents as insoluble compounds on the impregnated support in step (2) of the invention process is disclosed in U.S. Pat. No. 5,332,710 (incorporated herein by reference), and is described as a "rotation immersion" process.

In this alternative fixing procedure, the impregnated support from step (1) is immersed in the basic potassium salt solution and rotated or tumbled therein during the initial stages of the precipitation of the water-insoluble precious metal compounds. The rotation or tumbling of the support in the alkaline fixing solution preferably proceeds for at least about 0.5 hour upon the initial treatment and most preferably for at least about 2.5 hours. The rotation immersion treatment can be conducted up to about 4 hours before the treated support medium is allowed to stand in the fixing solution to insure that precipitation of the precious metal compounds is complete.

Any type of rotation or tumbling equipment can be utilized which provides a rotation action that is effective for contacting all of the support surfaces evenly with the basic potassium salt solution. The rotation action preferably is sufficiently gentle to prevent permanent loss of water-insoluble palladium and gold compounds from the catalyst support surface by abrasion.

The rotation immersion method is effective for achieving a thin shell coating of palladium and gold metals on the catalyst support surface with a controlled degree of thickness, e.g., a shell thickness between about 0.1–0.5 millimeters. For purposes of the present invention, a thin shell coating of palladium-gold metals on a catalyst support surface contributes to the improvement of carbon dioxide selectivity in vinyl acetate production from ethylene, acetic acid and oxygen.

Another fixing procedure in step (2) of the invention process is by an "incipient wetness" method. In this technique, a specific volume of aqueous basic potassium salt solution, equal to the absorptivity of the air-dried catalyst support medium from step (1) is applied to the support medium. The reactive admixture is allowed to stand until precipitation of the insoluble palladium and gold compounds is complete.

Another fixing procedure for step (2) of the invention process is described in U.S. Pat. No. 5,314,858, incorporated herein by reference. In this method, the step (2) fixing procedure is divided into at least two separate stages of support treatment with aqueous basic potassium salt solution.

Subsequent to the invention process step(2), the fixing stage by any of the methods described above, step (3) is performed. In step (3) the fixed support medium is washed repeatedly with deionized water to remove anions (e.g., chloride ions) which have been introduced by the impregnating solution in step (1) of the invention process. After the catalyst support medium is washed completely free of the anions, the catalyst is dried at a temperature up to about 150° C. under an inert atmosphere.

After the step (3) treatment is completed, in step (4) the catalyst support is contacted with a reducing agent to convert the fixed palladium and gold compounds into a shell coating of palladium and gold metal particles on the catalyst support surface. Illustrative of reducing agents are hydrazine, formaldehyde, ethylene, hydrogen, and the like.

If the reduction is performed with a solution of hydrazine hydrate, the reaction normally is conducted at ambient temperature. When the reduction is conducted in the gas phase with ethylene or hydrogen, it is advantageous to perform the reaction at an elevated temperature between about 100°–200° C. The reducing agent preferably is employed in excess to assure the complete conversion of the water-insoluble palladium and gold compounds into the free metal form. When hydrazine is employed, the weight ratio of hydrazine to precious metals ranges from about 10:1 to about 15:1. After the water-insoluble palladium and gold compounds have been reduced, the catalyst support is dried in an inert atmosphere at about 150° C.

Optionally, the present invention process for catalyst preparation can include an additional procedure (step (5)) to enhance the selectivity of the catalyst in vinyl acetate production. The palladium-gold catalyst obtained by the above-described process is treated with an aqueous solution of potassium alkanoate, and then dried. The potassium alkanoate content can be in the range between about 2–10 weight percent, based on the weight of the finished catalyst. Suitable potassium alkanoates include the potassium salt of formic acid, acetic acid, propionic acid, butyric acid, and the like.

Typically a present invention catalyst is employed in a vinyl acetate process by contacting ethylene, acetic acid and oxygen or air with a catalyst at temperatures between about 100°–200° C. and a pressure between about 1–10 atmospheres. The reaction usually is conducted with an excess of ethylene.

A present invention catalyst is characterized by a high level of palladium metal and gold metal retention, and exhibits improved selectivity in vinyl acetate production from ethylene, acetic acid and oxygen.

A present invention catalyst can provide efficient production of vinyl acetate, with a lower yield of carbon dioxide than conventional commercial-type vinyl acetate catalysts. The beneficial selectivity properties of the invention catalyst are attributable to the unique features of the present invention process for catalyst preparation, i.e., the exclusive use of sodium-free potassium salt derivatives in all the catalyst support impregnation steps.

The following examples are further illustrative of the present invention. The components and specific ingredients are presented as being typical, and various modifications can be derived in view of the foregoing disclosure within the scope of the invention.

The Vinyl Acetate Stirred Tank (VAST) Reactor in the Examples is a Berty reactor, or a continuous stirred tank reactor of the recirculating type that is run at constant oxygen conversion (about 45%). The catalyst (62 cc) is loaded in a basket in the reactor, a measured amount of acetic acid, ethylene, and oxygen is added in a nitrogen diluent, and the reactor is brought up to temperature by means of a heating mantle, and the temperature is measured above and below the catalyst. The reaction is terminated after approximately 18 hours at a temperature at which 45% oxygen conversion is maintained. Products are measured by gas-phase chromatography.

EXAMPLE I

This Example illustrates the preparation of a present invention Pd—Au catalyst by a standard method using potassium Pd—Au salts and potassium hydroxide as the fixing agent, and demonstrates the properties of the catalyst in the production of vinyl acetate from ethylene, acetic acid and oxygen in a VAST reactor system.

A 250 cc quantity of 5 mm silica spheres (KA-160, Sud Chemie) was impregnated with 87.29 mL of aqueous solution (5.13 g $K_2PdCl_4$ and 1.46 g $KAuCl_4$) to incipient wetness. The impregnated support was dried, and then treated with 87.29 mL of aqueous potassium hydroxide solution (2.62 g KOH), and the treated silica support was allowed to stand for about 16 hours. The silica support was washed with water until a negative $AgNO_3$ text was obtained.

The silica support was dried at 150° C. for about 16 hours under a nitrogen purge. The dried support was reduced with 5% ethylene in nitrogen at 150° C. for 5 hours. The reduced support was impregnated with 10 g of KOAc in 87.29 mL of water, and the resultant catalyst was dried in a fluid bed drier at 100° C. for one hour.

The Pd—Au catalyst as prepared had a weight content of 0.9% Pd, 0.32% Au, 8.2% KOAc, and 945 ppm Cl.

The properties of the invention Pd—Au catalyst for vinyl acetate production were determined in a VAST reactor, as summarized in Table A (Catalyst I).

EXAMPLE II

This Example illustrates the preparation of a present invention Pd—Au catalyst by a standard method using potassium Pd—Au salts and potassium hydroxide fixing agent, and demonstrates the properties of the catalyst in the production of vinyl acetate from ethylene, acetic acid and oxygen in a VAST reactor system.

Following the standard procedure of Example I, $K_2PdCl_4$ (5.13 g), $KAuCl_4$ (1.45 g), KOH (2.86 g) and KOAc (10 g) were employed.

After reduction with ethylene, the Pd—Au catalyst as prepared had a weight content of 1.0% Pd, 0.41% Au, 7.5% KOAc, and 1000 ppm Cl.

The properties of the invention Pd—Au catalyst for vinyl acetate production were determined in a VAST reactor, as summarized in Table A (Catalyst II).

A long term ageing test (23 months) indicated that a present invention type of all-potassium catalyst maintained a high activity level, and exhibited a low long term carbon dioxide selectivity in vinyl acetate production in comparison with commercial Pd—Au catalysts.

EXAMPLE III

This Example illustrates the preparation of a Pd—Au catalyst by a standard method using potassium Pd—Au salts and sodium hydroxide fixing agent, and demonstrates the properties of the catalyst in the production of vinyl acetate from ethylene, acetic acid and oxygen in a VAST reactor system.

Following the standard procedure of Example I, $K_2PdCl_4$ (5.13 g), $KAuCl_4$ (1.45 g), NaOH (2.04 g) and KOAc (10 g) were employed.

After reduction with ethylene, the Pd—Au catalyst as prepared had a weight content of 1.1% Pd, 0.46% Au, 7.7% KOAc, and 725 ppm Cl.

The properties of the Pd—Au catalyst for vinyl acetate production were determined in a VAST reactor as summarized in Table A (Catalyst III).

EXAMPLE IV

This Example illustrates the preparation of a Pd—Au catalyst by a standard method using sodium Pd—Au salts and sodium hydroxide fixing agent, and demonstrates the properties of the catalyst in the production of vinyl acetate from ethylene, acetic acid and oxygen in a VAST reactor system.

Following the standard procedure of Example I, $Na_2PdCl_4$ (1.65 g Pd), $NaAuCl_4$ (0.75 g Au), NaOH (1.766 g), and KOAc (10 g) were employed.

After reduction with ethylene, the Pd—Au catalyst as prepared had a weight content of 0.92% Pd, 0.38% Au, 7.98% KOAc, and 750 ppm Cl.

The properties of the Pd—Au catalyst for vinyl acetate production were determined in a VAST reactor, as summarized in Table A (Catalyst IV).

EXAMPLE V

This Example illustrates the preparation of a Pd—Au catalyst by a standard method using sodium Pd—Au salts and sodium hydroxide fixing agent, and demonstrates the properties of the catalyst in the production of vinyl acetate from ethylene, acetic acid and oxygen in a VAST reactor system.

Following the standard procedure of Example I, $Na_2PdCl_4$ (1.65 g Pd), $NaAuCl_4$ (0.75 g Au), NaOH (2.04 g), and KOAc (10 g) were employed.

After reduction with ethylene, the Pd—Au catalyst as prepared had a weight content of 0.89% Pd, 0.46% Au, 7.5% KOAc, and 770 ppm Cl.

The properties of the Pd—Au catalyst for vinyl acetate production were determined in a VAST reactor, as summarized in Table A (Catalyst V).

EXAMPLE VI

This Example illustrates the preparation of a present invention Pd—Au catalyst by a standard method using potassium Pd—Au salts and potassium silicate fixing agent, and demonstrates the properties of the catalyst in the production of vinyl acetate from ethylene, acetic acid and oxygen in a VAST reactor system.

Following the standard procedure of Example I, $K_2PdCl_4$ (1.65 g Pd), $KAuCl_4$ (0.75 g Au), $K_2SiO_3$ (2.0 g of K), and KOAc (10 g) were employed.

After reduction with ethylene, the invention Pd—Au catalyst as prepared had a weight content of 1.0% Pd, 0.44% Au, 7.6% KOAc, and 665 ppm Cl.

The properties of the invention Pd—Au catalyst for vinyl acetate production were determined in a VAST reactor, as summarized in Table A (Catalyst VI).

EXAMPLE VII

This Example illustrates the preparation of a Pd—Au catalyst by a standard method using sodium Pd—Au salts and potassium silicate fixing agent, and demonstrates the properties of the catalyst in the production of vinyl acetate from ethylene, acetic acid and oxygen in a VAST reactor system.

Following the standard procedure of Example I, $Na_2PdCl_4$ (1.65 g Pd), $NaAuCl_4$ (0.75 g Au), $K_2SiO_3$ (2.0 g of K), and KOAc (10 g) were employed.

After reduction with ethylene, the Pd—Au catalyst as prepared had a weight content of 0.98% Pd, 0.42% Au, 7.2% KoAc, and 910 ppm Cl.

The properties of the Pd—Au catalyst for vinyl acetate production were determined in a VAST reactor, as summarized in Table A (Catalyst VII).

EXAMPLE VIII

This Example illustrates the preparation of a Pd—Au catalyst by a standard method using sodium Pd—Au salts and sodium silicate fixing agent, and demonstrates the properties of the catalyst in the production of vinyl acetate from ethylene, acetic acid and oxygen in a VAST reactor system.

Following the standard procedure of Example I, $Na_2PdCl_4$ (1.65 g Pd), $NaAuCl_4$ (0.75 g Au), $Na_2SiO_3$ (7.23 g), and KOAc (10 g) were employed.

After reduction with ethylene, the Pd—Au catalyst as prepared had a weight content of 1.0% Pd, 0.44% Au, 7.4% KOAc, and 765 ppm Cl.

The properties of the Pd—Au catalyst for vinyl acetate production were determined in a VAST reactor, as summarized in Table A (Catalyst VIII).

EXAMPLE IX

This Example illustrates the preparation of a present invention Pd—Au catalyst by a rotation immersion method using potassium Pd—Au salts and potassium silicate fixing agent, and demonstrates the properties of the catalyst in the production of vinyl acetate from ethylene, acetic acid and oxygen in a VAST reactor system.

The procedure of Example I was followed to impregnate 5 mm silica spheres with 87.29 mL of aqueous solution (5.13 g $K_2PdCl_4$ and 1.46 g of $KAuCl_4$) to incipient wetness.

The impregnated support was treated with 300 mL of aqueous potassium silicate Solution (2.0 g of K). Following the procedure described in U.S. Pat. No. 5,332,710, the treated silica support was transferred to a rotation immersion flask, and the flask was rotated for 2.5 hours. The silica support then was washed until a negative $AgNO_3$ test was obtained.

The silica support was dried, and then reduced with 5% ethylene in nitrogen at 150° C. for 5 hours. The reduced support was impregnated with 10 g of KOAc in 87.29 mL of water, and the resultant invention catalyst was dried in a fluid-bed drier at 100° C. for one hour.

The invention Pd—Au catalyst as prepared had a weight content of 0.83% Pd, 0.34% Au, 7.8% KOAc, and 430 ppm Cl.

The properties of the invention Pd—Au catalyst for vinyl acetate product were determined in a VAST reactor, as summarized in Table A (Catalyst IX).

EXAMPLE X

This Example illustrates the preparation of a Pd—Au catalyst by a rotation immersion method using sodium Pd—Au salts and potassium silicate fixing agent, and demonstrates the properties of the catalyst in the production of vinyl acetate from ethylene, acetic acid and oxygen in a VAST reactor system.

Following the rotation immersion procedure of Example IX, $Na_2PdCl_4$ (1.65 g Pd), $NaAuCl_4$ (0.75 g Au), $K_2SiO_3$ (2.09 g of K), and KOAc (10 g) were employed.

After reduction with ethylene, the Pd—Au catalyst as prepared had a weight content of 0.94% Pd, 0.19% Au, 7.5% KOAc, and 1165 ppm Cl.

The properties of the Pd—Au catalyst for vinyl acetate production were determined in a VAST reactor, as summarized in Table A (Catalyst X).

The comparative data in Table A demonstrate that a Pd—Au catalyst prepared exclusively with potassium-containing reactants exhibits lower carbon dioxide selectivity in vinyl acetate production, in comparison with a corresponding Pd—Au catalyst which is prepared with one or more sodium-containing reactants.

The comparative data in Table A also demonstrate that a Pd—Au catalyst with potassium-containing reactants including potassium silicate fixing agent such as Catalyst IX, exhibits exceptional carbon dioxide selectivity improvement in the vinyl acetate process. The thin Pd—Au shell coating in Catalyst IX is a contributing factor in the carbon dioxide selectivity improvement, as compared to the Pd—Au catalyst with a thicker Pd—Au shell on the catalyst surface. The rotation immersion procedure provides a thinner Pd—Au shell which is beneficial for improvement of carbon dioxide selectivity.

Other important advantages derive from the use of potassium silicate as a fixing agent, in comparison with the use of potassium hydroxide. Potassium silicate is a mildly basic compound, and does not attack a silica support medium as does a strongly basic compound.

TABLE A

| Example Catalyst | Pd—Au Salts | Caustic Pd—Au Ratio | % Au | Fixing Agent | Pd—Au Shell mm | % Selectivity $CO_2$ | EtOAc | HE | Relative Activity |
|---|---|---|---|---|---|---|---|---|---|
| I | Potassium | 0.96:1 | 0.32 | KOH | 0.377 | 9.12 | 0.088 | 1.06 | 1.73 |
| II | Potassium | 1.04:1 | 0.41 | KOH | 0.352 | 9.40 | 0.097 | 1.27 | 2.00 |
| III | Potassium | 1.2:1 | 0.46 | NaOH | 0.409 | 9.95 | 0.096 | 1.45 | 2.18 |
| IV | Sodium | 1.04:1 | 0.38 | NaOH | N.A. | 10.24 | 0.073 | 1.02 | 1.81 |
| V | Sodium | 1.2:1 | 0.46 | NaOH | 0.497 | 10.21 | 0.084 | 1.20 | 2.05 |
| VI | Potassium | 1.2:1 | 0.44 | $K_2SiO_3$ | 0.232 | 9.48 | 0.093 | 1.43 | 2.16 |
| VII | Sodium | 1.2:1 | 0.42 | $K_2SiO_3$ | 0.216 | 11.45 | 0.087 | 1.22 | 1.97 |
| VIII | Sodium | 1.2:1 | 0.44 | $Na_2SiO_3$ | 0.419 | 10.60 | 0.083 | 1.17 | 2.11 |
| IX | Potassium | 1.2:1 | 0.24 | $K_2SiO_3$ | 0.129 | 8.13 | 0.106 | 1.13 | 1.58 |
| X | Sodium | 1.2:1 | 0.19 | $K_2SiO_3$ | 0.103 | 9.67 | 0.087 | 0.94 | 1.12 |

What is claimed is:

1. A process for the preparation of a catalyst for production of vinyl acetate from ethylene, acetic acid and oxygen, which process comprises (1) impregnating a porous catalyst support medium with an aqueous solution consisting essentially of water-soluble potassium-palladium compound and water-soluble potassium-gold compound; (2) precipitating water-insoluble palladium and gold compounds onto the catalyst support surfaces with an aqueous solution of basic potassium salt fixing agent; and (3) reducing the water-insoluble palladium and gold compounds to palladium metal and gold metal to form a catalyst with improved carbon dioxide selectivity.

2. A process in accordance with claim 1 wherein the catalyst support medium in step (1) is a silica substrate.

3. A process in accordance with claim 1 wherein the catalyst support medium in step (1) is an alumina substrate.

4. A process in accordance with claim 1 wherein the catalyst support medium in step (1) is in the form of spherical structures.

5. A process in accordance with claim 1 wherein the catalyst support medium in step (1) is in the form of tablets.

6. A process in accordance with claim 1 wherein the catalyst support medium in step (1) is in the form of Raschig rings.

7. A process in accordance with claim 1 wherein the potassium-palladium compound and the potassium-gold compound in step (1) are applied in the same aqueous solution or successively in separate aqueous solutions.

8. A process in accordance with claim 1 wherein the potassium-palladium compound in step (1) is potassium palladium tetrachlorate ($K_2PdCl_4$).

9. A process in accordance with claim 1 wherein the potassium-gold compound in step (1) is potassium tetrachloroaurate ($KAuCl_4$).

10. A process in accordance with claim 1 wherein the basic potassium salt in step (2) is selected from the group consisting of potassium hydroxide, potassium carbonate and potassium metasilicate.

11. A process in accordance with claim 1 wherein the precipitating and fixing of water-insoluble palladium and gold compounds in step (2) includes a rotation immersion procedure.

12. A process in accordance with claim 11 wherein the catalyst product is characterized by a palladium-gold metal shell having a thickness of about 0.1 to 0.5 millimeters on the support surface, and the catalyst provides improved carbon dioxide selectivity in vinyl acetate production.

13. A process in accordance with claim 1 wherein the reduction of palladium and gold compound in step (3) is with ethylene or hydrazine reducing agent.

14. A process in accordance with claim 1 wherein the catalyst product has a palladium metal content between about 0.4–2.5 weight percent, and a gold metal content between about 0.1–1.0 weight percent, based on the catalyst weight.

15. A process in accordance with claim 1 wherein the catalyst product has a palladium:gold weight ratio between about 1–10:1.

16. A process in accordance with claim 1 where in an additional procedure the catalyst product is impregnated with an aqueous solution consisting essentially of a potassium alkanoate activator, and then dried to provide a catalyst product with enhanced carbon dioxide selectivity for vinyl acetate production.

17. A process in accordance with claim 16 wherein the activator additive is potassium acetate.

18. A process in accordance with claim 16 wherein all of the support-impregnating reactants are essentially sodium-free.

19. A catalyst composition for the production of vinyl acetate from ethylene, acetic acid and oxygen, prepared in accordance with the process of claim 1.

20. A catalyst composition for the production of vinyl acetate from ethylene, acetic acid and oxygen, prepared in accordance with the process of 16.

* * * * *